United States Patent [19]

Whittle

[11] Patent Number: 4,632,758
[45] Date of Patent: Dec. 30, 1986

[54] ANAEROBIC WASTEWATER TREATMENT SYSTEM

[75] Inventor: Thomas E. Whittle, Harrisburg, Pa.

[73] Assignee: Commonwealth Engineering & Technology, Inc., Harrisburg, Pa.

[21] Appl. No.: 773,840

[22] Filed: Sep. 6, 1985

[51] Int. Cl.$^4$ .............................. C02F 3/28; C12P 5/02
[52] U.S. Cl. .................................... 210/603; 210/612; 210/151; 210/180; 210/188; 210/218; 210/195; 48/111; 435/167; 435/316
[58] Field of Search ............... 210/603, 612, 613, 188, 210/194, 150, 151, 218, 195.3, 180, 614; 48/197 S, 111; 435/167, 316, 801

[56] References Cited

U.S. PATENT DOCUMENTS

| | | |
|---|---|---|
| 2,360,811 | 10/1944 | Kelly et al. . |
| 2,638,444 | 5/1953 | Kappe .................................. 210/603 |
| 2,777,815 | 1/1957 | Forrest . |
| 2,786,025 | 3/1957 | Lamb et al. . |
| 3,232,865 | 2/1966 | Quinn et al. . |
| 3,371,033 | 2/1968 | Simmons et al. . |
| 3,402,103 | 9/1968 | Amberg et al. ...................... 210/151 |
| 3,623,976 | 11/1971 | Cessna ................................. 210/151 |
| 3,715,304 | 2/1973 | Hefermehl ........................... 210/180 |
| 3,838,199 | 9/1974 | Coe et al. ............................. 210/603 |
| 4,092,338 | 5/1978 | Tossey ................................. 210/175 |
| 4,203,838 | 5/1980 | Shimizu et al. ..................... 210/603 |
| 4,231,863 | 11/1980 | Sutphin ............................... 210/615 |
| 4,284,508 | 8/1981 | Jewell ................................... 210/603 |
| 4,297,216 | 10/1981 | Ishida et al. ......................... 210/603 |
| 4,303,517 | 12/1981 | Love et al. ........................... 210/208 |
| 4,311,593 | 1/1982 | Benjes et al. ........................ 210/603 |
| 4,366,059 | 12/1982 | Witt et al. ............................ 210/615 |
| 4,530,762 | 7/1985 | Love .................................... 210/188 |
| 4,532,042 | 7/1985 | Aivasidis et al. .................... 210/614 |

FOREIGN PATENT DOCUMENTS

| | | | |
|---|---|---|---|
| 2913034 | 10/1980 | Fed. Rep. of Germany ...... 210/603 |
| 3304365 | 8/1984 | Fed. Rep. of Germany ...... 210/603 |
| 59-166295 | 9/1984 | Japan ................................... 210/603 |

*Primary Examiner*—Benoît Castel
*Attorney, Agent, or Firm*—Neuman, Williams, Anderson & Olson

[57] ABSTRACT

An anaerobic apparatus for treating wastewater is disclosed. The treating apparatus comprises a reactor housing a media having a plurality of surfaces for receiving bacteria. The wastewater that is to be treated, is introduced into the bottom of the reactor and forced up over the surfaces of the media, whereby the bacteria on the surfaces of and in the voids of the media consume the organic materials in the wastewater by an anaerobic digestion process to produce methane and a biological sludge. The biological sludge is collected and stored in a bottom storage portion of the reactor, whereby further digestion occurs to condense the mass of such sludge. A first conduit array is disposed above the media for withdrawing the treated wastewater. A second conduit array is disposed in communication with the storage portion for withdrawing biological sludge from the reactor.

13 Claims, 5 Drawing Figures

ANAEROBIC WASTEWATER TREATMENT SYSTEMbs

BACKGROUND OF THE INVENTION

1. Field of the Invention

The present invention relates to the treatment of wastewater or sewage to remove impurities therefrom.

2. Description of the Prior Art

There are a large number of industries which, because of the nature of the product thereof, produce a wastewater which is very high in organic constituents and is generally not acceptable for disposition in a lake, a river or the like because of the high oxygen demand associated therewith. In particular, environmental laws and regulations are becoming increasingly stringent in requiring the removal of chemical and biological oxygen demanding substances (COD and BOD) from wastewater before such water is allowed to flow into public water ways. An example of such a wastewater is the effluent from a food processing plant. In such a plant, water is used in the preparation or processing of fresh vegetables and other manufactured food items, as well as for steam generation and sanitary facilities. Before the water used in such processing may be discharged, the waste deposited during processing must be removed to a degree that will satisfy the various, imposed environmental laws and regulations.

The prior art has suggested a number of devices and processes for removing impurities or waste from the wastewater so as to improve the quality thereof. Such devices have included reactors and clarifiers, and such processes have included both aerobic and anaerobic processes.

In a typical aerobic process, the wastewater is directed through a reactor vessel with microorganisms therein and is thereafter passed into a settling basin. An underflow from the settling basin is then returned to the reactor vessel. In the course of such process, the wastewater is mixed with large quantities of organisms and air. Microorganisms use the organic waste for food, and use the oxygen in the air to burn a portion of this food to produce carbon dioxide and water for energy. Since these organisms obtain much energy from the oxidation, their growth is rapid and a large portion of the organic waste is converted into new cells. The portion converted to cells is not actually stabilized, but is simply changed in form. Although the cells can be removed from the waste stream, the biological sludge they produce still presents a significant disposal problem.

In the anaerobic process, wastewater is injected into a reactor vessel and contacted with sludge containing microorganisms. Effluent leaving the reactor vessel is passed through a degassifier and into a settling tank. Heavier sludge falls to the bottom of the settling tank and is recirculated to the reactor vessel. Waste water is also mixed with large quantities of organisms, but unlike the aerobic process, air is excluded. Under these conditions, bacteria grow which are capable of converting the organic waste to carbon dioxide and methane gas. Unlike aerobic oxidation, the anaerobic conversion to methane gas yields relatively little energy to the microorganisms. Thus their rate of growth is slow and only a small portion of the waste is converted to new cells, the major portion of the degradable waste berng converted to methane gas. Such conversion to methane gas represents waste stabilization, since this gas is insoluble and escapes from the waste stream where it can be collected and burned. The prior art has recognized that the biproduct of methane gas is a good source of fuel energy and has used same for heating buildings, running engines, and producing electricity.

The anaerobic treatment process does have a number of disadvantages. The major disadvantage is that relatively high temperatures are required for optimum operation; temperatures in the range of 85° to 95° F. are preferred. Another disadvantage of anaerobic treatment is related to the slow rate of growth of the methane producing bacteria. As a result, longer periods of time are required for starting the process. The slow rate of growth also limits the rate at which the process can adjust to changing waste loads, temperatures and other environmental conditions. Further, the gas produced in anaerobic treatment makes the suspended particles buoyant and difficult to settle. Therefore, a degassifier is frequently required between the digester and the settling tank in the anaerobic contact process to permit proper settling of the suspended solids.

U.S. Pat. No. 4,311,593 of Benjes et al. discloses an anaerobrc reactor or biological digester, where effluent in the form of wastewater from the production of alcoholic beverages is introduced at the top of the reactor and, then, flows downward through a media. Sloughed biomass along with a portion of the wastewater is collected at the floor of the digester and is recirculated by a pump to be reintroduced at the top of the reactor to engage and interact with the digester influent. Methane is collected at the top of the digester and is conducted to a combuster, where the methane is burned to produce heat for the distilling the fermented molasses. Further, effluent may be removed from the digester at its lower end and forced by a pump to a waste disposal.

U.S. Pat. No. 2,360,811 of Kelly et al. discloses a purification system where wastewater is successfully processed by a screening station, a grit washing station, a gas diffusing station, a vacuum flotation apparatus, wherein settling of large solid particles occurs and, finally, a biological digester. A burnable gas is collected at the top of the digester and is conducted to an incinerator, where sludge is heated to form sludge cakes. Digested sludge is removed from the bottom of the biological digester and is directed through a dewatering station for sludge filtering. Filtrate from the dewatering station and supernatant from the digester are reinserted into the process ahead of the gas diffusing station. The wastewater is introduced into the biological digester and is directed downward through its media.

U.S. Pat. No. 3,623,976 of Cessna discloses the recirculation of sludge collected in a bottom portion of an activated biological filter. In a first recirculation path, effluent is taken from the bottom of the biological filter and is passed through a clarifier before being pumped into a top portion of the biological filter. In a second path, effluent is taken directly from the bottom portion of the filter and is recirculated to the top thereof. Alternatively, Cessna permits sludge to be taken from the clarifier and discharged as waste.

U.S. Pat. No. 4,366,059 of Witt et al. discloses an anaerobic treatment plant including a biological filter. Particles of solid biomass are withdrawn from the filter and recycled to the base of the filter together with fresh acidic waste and added inorganic alkaline material. Witt et al. suggests that the alkaline material may be magnesium oxide or sodium formate.

SUMMARY OF THE INVENTION

In accordance with these and other objects of the invention, there is provided an anaerobic apparatus for treating wastewater. The treating apparatus comprises a reactor housing a media having a plurality of surfaces for receiving bacteria. The wastewater that is to be treated, is introduced into the bottom of the reactor and forced up over the surfaces of the media, whereby the bacteria on the surfaces of and in the voids of the media consume the waste in the wastewater by an anaerobic digestion process to produce methane and a biological sludge. The biological sludge produced is removed in a clarifier and introduced into the bottom of the reactor and into a storage portion, whereby the biological sludge may be collected and stored, whereby further digestion occurs to condense the mass of such sludge. Means in the form of a conduit array is disposed above the media for withdrawing the treated wastewater. Means in the form of another conduit array is disposed in communication with the storage means for withdrawing biological sludge from the reactor.

In a further aspect of this invention, the methane given off as a bi-product of the anaerobic digestion process, is used as a source of fuel for heating the reactor influent immediately before it is introduced into the reactor. Further, the treatment apparatus of this invention may be associated with a plant that gives off heated water, which is utilized to heat further the reactor influent.

In a still further aspect of this invention, the reactor effluent is directed to a degassifier, whereby entrained gas is released, before introducing the degassified reactor effluent into a clarifier, whereby the effluent's biological sludge may settle out. A conduit extracts the biological sludge from the clarifier and introduces it into the reactor. The recirculated biological sludge may be mixed with the waste water before being introduced into the reactor at a point intermediate the bottom storage portion and the media or, alternatively, the sludge may be directed to the storage portion directly. In addition, the reactor effluent may be extracted before it is degassified to be recirculated and reintroduced into the reactor.

In a still further aspect of this invention, the treatment apparatus includes a source of an alkaline substance such as bicarbonate for introducing a bicarbonate slurry in an amount sufficient to enhance the activity of the methane producing bacteria, but insufficient to effect directly the pH of the reactor contents.

BRIEF DESCRIPTION OF THE DRAWINGS

A detailed description of the preferred embodiment of this invention is hereafter made with specific reference to the drawings, in which.

DETAILED DESCRIPTION OF A PREFERRED EMBODIMENT

Figure 1:
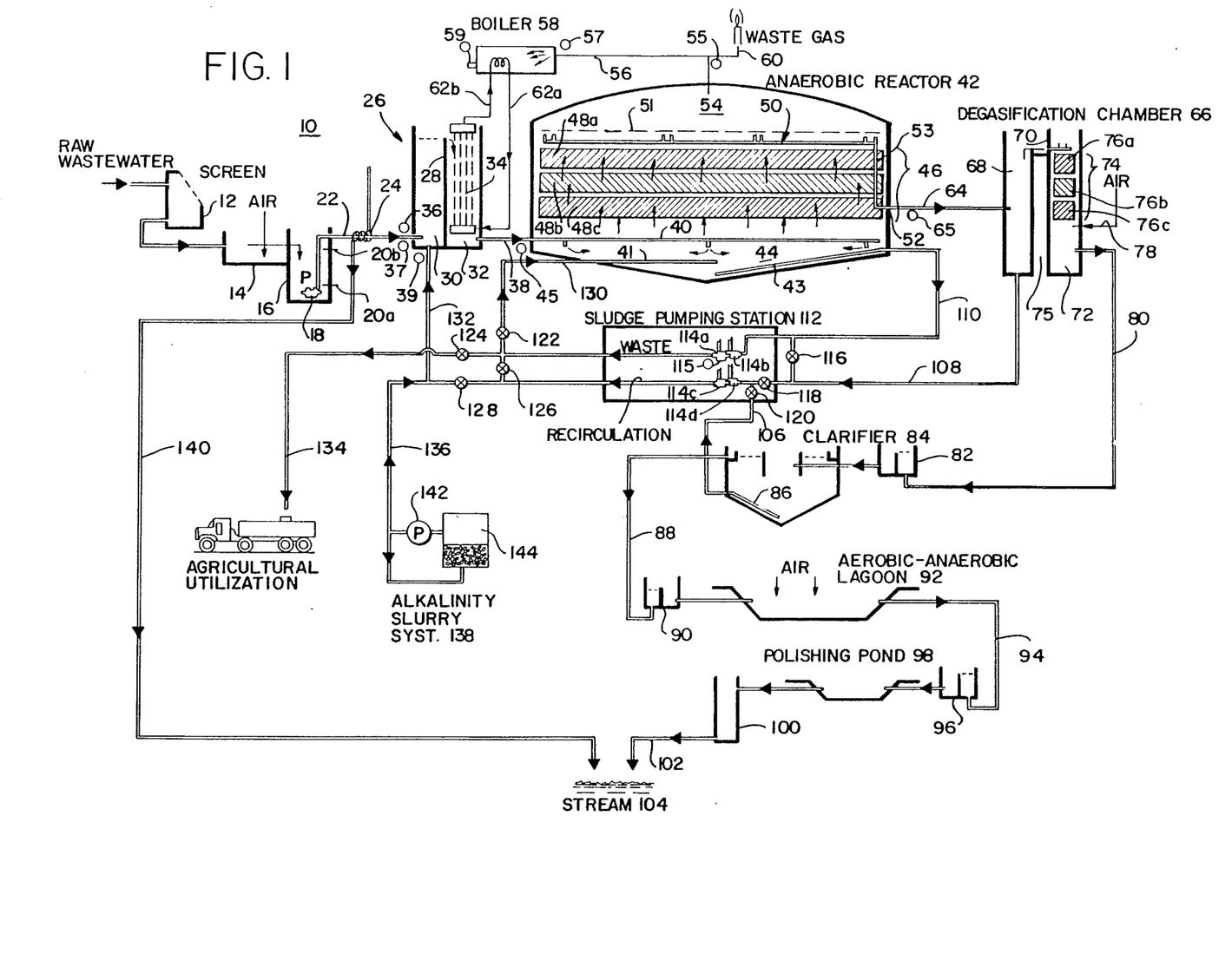
FIG. 1 is a schematic diagram of the anaerobic wastewater treatment system in accordance with teachings of this invention.

With reference to drawings and, in particular, to FIG. 1, an anaerobic wastewater treatment system 10 is shown wherein wastewater as derived from a food processing plant, where water is used in the preparation and processing of fresh vegetables, dry beans, tomato products, and other manufactured food items, is treated to remove waste therefrom to a degree to meet the applicable environmental laws and regulations, before such wastewater is discharged into a receiving stream 104. Influent in the form of the food processing plant's raw wastewater is introduced through a screen 12, an aerated grit chamber 14, a supplemental heat exchanger 24 and a primary heat exchanger 34, into an anaerobic reactor 42.

Wastewater from the food processing plant first flows through a coarse bar screen (not shown) disposed in front of the screen 12. The coarse bar screen removes cans, boards, and other large items that may block the systems conduits or otherwise interfere with the subsequent treatment units. The screen 12 includes static screens for removal of vegetable scraps and similar materials. Illustratively, three static screens, each with a hydraulic capacity of 600 gallons per minute are utilized. Next, the screened wastewater will flow into the aerated grit chamber 14, where small inorganic particles will be removed. Illustratively, the aerated grit chamber 14 has a liquid capacity of 5,130 gallons, which will provide a minimum hydraulic detention time of three minutes at a flow rate of 2.5 MGD. The aerated grit chamber 14 includes a grit screw (not shown) to collect the grit at one end of the aerated grit chamber 14; thereafter the grit is airlifted to a dewatering screw, which will discharge the grit onto a conveyor belt. The conveyor belt, in turn, carries the grit as well as the screenings out of the aerated grit chamber 14. The wastewater flows out of the aerated grit chamber 14 into a wet well 16 containing illustratively four submerged wastewater pumps 18. These pumps 18 lift the processed wastewater to the following biological treatment units. The wet well 16 has high and low level probes 20b and 20a, respectively, which provide signals to plant personnel indicative of the failure of the pumps 18 or a mismatch between pump output and inputted wastewater flow.

The temperature of the processed wastewater is brought to the mesophilic range of 85° to 100° F. by a first or supplemental heat exchanger 24 and a second or primary heat exchanger 34. The processed wastewater is pumped out of the wet well 16 and through a conduit 22. The supplemental heat exchanger 24 is disposed about the conduit 22 in a heat exchange relationship and uses the non-contact cooling water derived from the food processing plant as the heat source. Typically, the temperature of the non-contact cooling water as supplied to the supplemental heat exchanger 24 is in the order of 110° F., whereby the temperature of the processed wastewater is raised by approximately 10° F. After supplying heat through the supplemental heat exchanger 24, the non-contact cooling water passes through a discharge conduit 140 to be discharged into the receiving stream 104. The processed wastewater is discharged from the conduit 22 into an influent chamber 26 and, in particular, into an input well 30, before overflowing into a second or heating well 32. A partition 28 divides the influent chamber 26 into the input well 30 and a heating well 32. The primary heat exchanger 34 is disposed within the heating well 32, wherein the temperature of the processed wastewater is raised in a controlled manner to the optimum range. As will be explained, methane gas produced as a bi-product of the anaerobic treatment process, is extracted from the anaerobic reactor 42, thus serving as a source of fuel for the heat exchanger 34. The heated wastewater is taken from the heating well 32 and is passed via the input conduit 38 into the anaerobic reactor 42.

As shown generally in FIG. 1 and more specifically in FIGS. 2 and 3, the anaerobic reactor 42 includes an influent distribution conduit array 40 for introducing the wastewater below a cross-flow plastic media assembly 46 of the anaerobic reactor 42. As shown particularly in FIG. 3, a conduit 39 is coupled to conduit 38 and extends to the center of the array 40 and is connected thereto by a coupling 41, whereby more even distribution of the wastewater is achieved. Significantly, the wastewater is forced up through the media assembly 46, a honeycombed type of structure. As will be discussed in detail below, anaerobic bacteria, in the voids and on the many surfaces of the media assembly 46, breakdown the organic pollutants in the wastewater giving off methane gas. The methane gas passes up through and escapes from the wastewater, into an upper collection chamber 54 of the anaerobic reactor 42. The methane gas is collected and stored within the chamber 54 and is selectively supplied via a gas conduit 56 to a boiler 58, which serves to heat recirculating water before it is directed via a water circulation conduit 62a to the primary heat exchanger 34, before being returned to the boiler 58 via water circulation conduit 62b.

The heart of the anaerobic reactor 42 is the crossflow plastic media assembly 46, which provides a large surface area and void volume for anaerobic bacteria. As shown in FIGS. 1, 2 and 3, the media assembly 46 comprises a top media 48a, a middle media 48b and a lower media 48c. Each media 48 comprises an array of surfaces over which the processed wastewater flows as indicated by the arrows in FIG. 2 and 3. The wastewater fills the anaerobic reactor 42 to a water level 51. An effluent collection conduit array 50 collects and draws off the wastewater to be directed via a coupling conduit 53, an outlet 52 and an output conduit 64 to a degassification chamber 66. As particularly illustrated in FIG. 3, sludge 174 is introduced and/or builds up within the bottom or storage portion 44 of the anaerobic reactor 42. The efficiency of the bacteriological process carried out by the anaerobic reactor 42 increases at a relatively slow rate over a relatively long start-up period until the process has stabilized and the mass of the biological sludge 174 collected within the storage portion 44 builds up to a critical level with respect to the flow rate and mass of the process wastewater flowing through the anaerobic reactor 42. As will be explained in detail later, sludge may be introduced via sludge introduction conduit 41 and withdrawn via sludge withdraw conduit 43.

The reactor effluent, including some biological sludge, is discharged from the reactor 42 and is conveyed via outlet conduit 64 to the degassification chamber 66, which removes any remaining gas in the sludge which would otherwise interfere with the subsequent removal of the sludge from the wastewater. As generally indicated in FIG. 1, the degassified wastewater is passed via conduit 80 and a distribution box 82 to a clarifier 84, which removes the remaining biological sludge. The degassification chamber 66 includes a wet well 68 for initially receiving the reactor effluent, before passing it to a degassing chamber 72. As will be explained with respect to FIGS. 4 and 5, the degassification chamber 66 includes an effluent weir 70 that is raised and lowered to control the water level not only within the degassification chamber 66, but also the water level 51 within the anaerobic reactor 42. As the reactor effluent flows over the effluent weir 70, it is distributed over a media assembly 74 comprised of three sections 76a, 76b and 76c. The raising and lowering of the effluent weir 70 also compensates for gas pressure variations within the anaerobic reactor 42. The media assembly 74 thin-films the reactor effluent, thereby facilitating the release of gas trapped in the wastewater prior to introduction into the clarifier 84. The aeration provided by the wastewater flowing through the media assembly 74 and the associated temperature drop, also serves to release entrained gas. The clarifier 84 essentially removes the remaining biological sludge. The clarifier 84 is conventional and is provided with sludge hoppers disposed at its bottom, a rake mechanism, and surface skimming capabilities. Although recirculation will normally be pumped through the degassification chamber 66, the clarifier 84 is sized to allow recirculation from its sludge hopper. Sludge may be withdrawn from the bottom of the clarifier 84 by a sludge collecting conduit 86.

Clarified effluent is directed from the clarifier 84 via a conduit 88 for further treatment in an aerobic-anaerobic stabilization lagoon 92. In the aerobic-anaerobic lagoon 92, the following three zones exist: (1) a surface zone where aerobic bacteria and algae exists in symbiotic relationship; (2) an anaerobic bottom zone in which settled solids are decomposed by anaerobic bacteria; and (3) an intermediate zone that is partly aerobic and partly anaerobic, where decomposition is accomplished by facultative bacteria. Surface aeration is provided to maintain aerobic conditions in the top layer of the lagoon 92. Although sufficient aeration is provided to satisfy the organic loading on the lagoon 92, the power input from the aerators must be less than those required for mixing in order to maintain the anaerobic lower zone.

Wastewater is transferred from the lagoon 92 via a conduit 94 to a polishing pond 98 for final treatment, before being discharged into the receiving stream 104. The wastewater discharged into the stream 104 meets the applicable ecological regulations and laws. The polishing pond 98 allows quiescent settling of the lagoon effluent prior to discharge into the receiving stream 104. The level of the pond 98 is fixed. Aeration of the pond content will be by the air-water interface and also will occur as the effluent passes into an output chamber 100, before being passed via conduit 102 into the stream 104.

The operating parameters of the biological process carried on within the anaerobic reactor 42 include the temperature of the reactor effluent, as well as the mass of the collected biological sludge stored in the bottom portion 44 of the anaerobic reactor 42. The quantity of biological sludge and, in part, the temperature of the reactor influent is controlled by recirculating the reactor effluent and/or biological sludge to be reintroduced into the bottom of the anaerobic reactor 42. Bacterial sludge as collected in the bottom of the clarifier 84 is discharged via sludge collection conduit 86 and directed via conduit 106 to a sludge pumping station 112, whereby it is directed via a series of valves 126 and 122

(values 124 and 128 being closed) and conduit 130 to be injected by the sludge introduction conduit 41 into the bottom portion 44 of the anaerobic reactor 42. Alternatively, the sludge may be directed from the sludge pumping station 112 via opened valve 128 (valve 126 being closed) and recirculating conduit 132 into the input well 30 of the influent chamber 26, to be mixed with the raw wastewater before being reintroduced via conduit 38 and the influent distribution conduit array 40 into the anaerobic reactor 42. During start-up of the wastewater treatment system 10 when it is desirable to enhance the efficiency of the bacteriological process, it may be desirable to recirculate the bacterial sludge with the raw wastewater. After the start-up, typically requiring six months to a year of operation, it is normally desired to introduce the bacterial sludge via the sludge introduction conduit 41 directly into the bottom 44 of the anaerobic reactor 42, for storage, and further volume reduction of the sludge through digestion. In this manner, the bacterial sludge will be feed to the bottom portion 44 without interfering with the reactor influent as introduced by the influent distribution conduit array 40. As illustrated in FIGS. 1 and 3, the sludge introduction conduit 41 is disposed approximately 6 ft. below the influent distribution conduit array 40. Illustratively, the volume available in the bottom portion 44 for bacterial sludge storage is 228,700 gallons. At the expected sludge production rate 0.08 lbs TSS/lb. biochemical oxygen demand (BOD) applied and a sludge concentration of 3% TSS as derived from the clarifier 84, a hydraulic detention time for sludge of 100 days is available. Assuming that the sludge 174 will thicken to 5% TSS in the bottom portion 44 of the anaerobic reactor 42, a solids retention time of 170 days is expected.

Excess bacterial sludge is discharged from the bottom storage portion 44 of the anaerobic reactor 42 via the sludge withdrawal conduit 43, the recirculating conduit 110, the sludge pumping station 112 (control valve 116 being closed), opened control valve 124 (control valves 122 and 126 being closed) and conduit 134. As suggested in FIG. 1, such sludge has potential agricultural utilization. The sludge pumping station 112 includes a pair of sludge pumps 114a and 114b associated with conduit 110 for pumping waste either to conduit 134 for discharge or via opened control valve 122, conduit 130 and the sludge introduction conduit 41 into the bottom portion 44 of the anaerobic reactor 42. Further, the sludge pumping station 112 includes a second pair of pumps 114c and 114d associated with control valves 118 and 120. By opening control valve 120 and closing control valve 118, sludge from the clarifier 84 may be recirculated. By closing control valve 120 and opening control valve 118 reactor effluent may be recirculated directly from the degassification chamber 66 via the conduit 108, the sludge pumping station 112, the opened control valve 128, and conduit 132 into the influent chamber 26, before being reintroduced via the influent distribution conduit array 40 into the anaerobic reactor 42. By recirculating the reactor effluent prior to degassification and clarification, the heat losses associated with these operations are minimized and the temperature of the recirculated effluent is maintained at a higher level than if the effluent is passed through the degassification chamber 66 and the clarifier 84 before being reintroduced into the anaerobic reactor 42; in this fashion, the bacteria population within the anaerobic reactor 42 is maintained at substantially the same level.

The anaerobic wastewater treatment system 10 includes an alkalinity slurry system 138 to introduce a bicarbonate such as soda ash, sodium bicarbonate or sodium sesquicarbonate, into the process wastewater within the influent chamber 26 to maintain the alkalinity in the anaerobic reactor 42. The alkalinity slurry system 138 meters the selected bicarbonate into the conduit 136 using a rotameter off of the alkalinity circulation line. A reservoir 144 stores the bicarbonate, a pump 142 circulates the water through the bicarbonate slurry and a rotameter 141 to direct selectively a portion of the slurry, i.e., a controlled amount of bicarbonate, via conduits 136 and 132 into the input well 30 of the influent chamber 26, to maintain the volatile acid/alkalinity ratio of the reactive contents within a specified range. In particular, grab samples are taken of the effluent from the reactor 42, typically at the point where the effluent overflows the effluent weir 70. A volatile acids and an alkalinity test, each well known in the art, is made of the sample to determine the amount in milligrams per liter of the volatile acids, as well as the alkaline substance expressed in terms of milligrams per liter of calcium carbonate. The volatile acids test provides a measurement of the organic acids present in the wastewater. Volatile fatty acids are classified as water-soluble fatty acids that can be distilled at atmospheric pressure. The straight distillation method is suitable for a control test for anaerobic digestion. The amount of volatile acids and the equivalent amount of calcium carbonate are used to determine the ratio thereof. Generally if the ratio of volatile acids to the equivalent calcium carbonate is less than 0.2, the process is considered to have a sufficiently high buffer capacity to handle the production of volatile acids, whereby the pH is maintained in the desired range and, as a result, the methane producing bacteria are active to facilitate the conversion of waste products to methane. These measurements are made daily, typically, and a change of the activity will be apparent. Generally less than 0.2. The pH of the reactor effluent is also monitored by grab sampling, at the point the effluent overflows the weir 70. The pH measurement verifies that the anaerobic process carried out by the reactor 42 is functioning well and that the pH is being maintained in the proper range of 6.8 to 7.2. However, if the volatile/alkalinity ratio approaches and exceeds 0.2, then the pump 142 and the rotor meter is activated to deliver a sufficient amount of calcium carbonate via conduits 136 and 132 into the reactor 142. The introduction of the bicarbonate to maintain alkalinity will also maintain pH in the optimum range. As will be explained, the dosage rate is effected by the natural production of alkalinity in the anaerobic process.

Measurement of the raw wastewater flow to the anaerobic wastewater treatment system 10 is made by a flow meter 37 of the doppler type, installed to measure the wastewater flowing through the conduit 22 prior to its introduction into the influent chamber 26. The output of the flow meter 37 also provides an indication of the treated wastewater discharged to the receiving stream 104. A second flow meter 39 is installed to measure the fluid flowing through the recirculation conduit 132 and into the influent chamber 26. Though not shown, signals provided by the flow meters 37 and 39 are connected to flow meter recorders located in a centrally disposed control room. Stroke counters 115 are mounted on the sludge pumps 114a and b to provide an indication of sludge flow from the sludge pumping station 112, as a product of the stroke count and the volume of the pump's bore.

The production or flow of methane from the anaerobic reactor 42 is monitored by a gas meter 55 associated with the output gas conduit 56. Similarly, a gas meter 57 measures the gas flow through conduit 56 into the boiler 58. Gas burned in the waste gas burner 60 is determined by taking the difference between gas leaving the anaerobic reactor 42 and that utilized in the boiler 58. Manometers (not shown) are provided to indicate gas pressure in the conduit 56 leaving the reactor 42 to insure that the methane entering the boiler 58 is of sufficient pressure to be burned.

A temperature probe 36 is disposed to measure the temperature of the raw wastewater flowing through the conduit 32 immediately prior to its introduction into the influent chamber 26. A second temperature probe 45 is associated to measure the temperature of the water as heated by the primary heat exchanger 34 and passing through the conduit 38 prior to its introduction into the anaerobic reactor 42. A third temperature probe 65 is disposed to measure the temperature of the reactor effluent prior to its being introduced into the degassification chamber 66. The operation of the heat exchanger 34 is automatically controlled by the output of the temperature probe 45. The temperature probe 45 measures the temperature of the wastewater introduced by conduit 38 into the reactor 42. The temperature measured by probe 45 is compared with a set point set to maintain the temperature of the wastewater in the anaerobic reactor 142 within the mesophilic range of 85° to 100° F. and, preferably, in the range of 90° to 95° F. If the temperature falls below the particular set point, a pump 61 disposed within the closed loop comprised of conduits 62a and 62b for exchanging water between the boiler 58 and the heat exchanger 34, is actuated to thereby heat the wastewater until its temperature is again above the desired set point. A second temperature probe 64 measures the temperature of the effluent discharge from the anaerobic reactor 42 to determine the temperature drop of the wastewater as it is processed within the anaerobic reactor 42. The temperature drop depends primarily upon the ambient temperature and, in the winter, this temperature drop can increase. At such times, the set point will be increased to maintain the temperature of the wastewater within the anaerobic reactor 42 within the desired range.

As noted above, there are two heating systems, i.e., a supplemental heat exchanger 24 and the primary heat exchanger 34, which heats the reactor influent to maintain the temperature of the reactor content within the mesophilic range, i.e., 85° to 100° F. The supplemental heat exchanger 24 is used primarily when the food processing plant is operative to provide the cooling water of elevated temperature as a bi-product of the food processing. However, during periods that the food processing plant is not operative, the biological process within the anaerobic reactor 42 must continue and the reactor influent must be heated to the desired range by the primary heat exchanger 34. During those periods when the cooling water from the food processing plant is not available and the temperature of the influent introduced into the influent chamber 26 decreases, the temperature probe 45 is operative to sense the decrease of temperature to actuate the operation of the boiler 58, as explained above.

Figure 2:
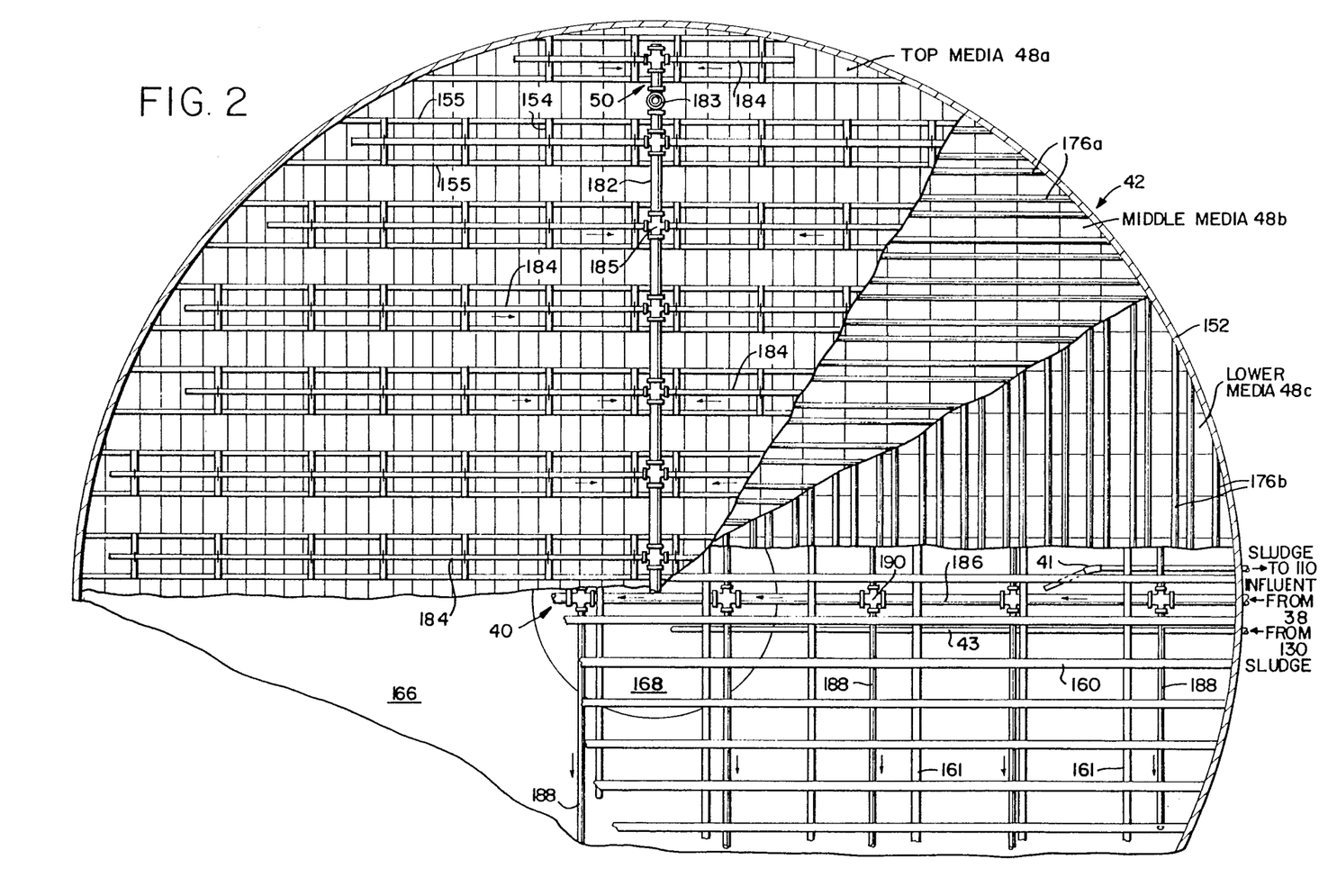
FIG. 2 is a top view showing the anaerobic reactor of the system shown in FIG. 1, with various parts broken away to show sections of increasing depth as viewed from the top thereof.
Figure 3:
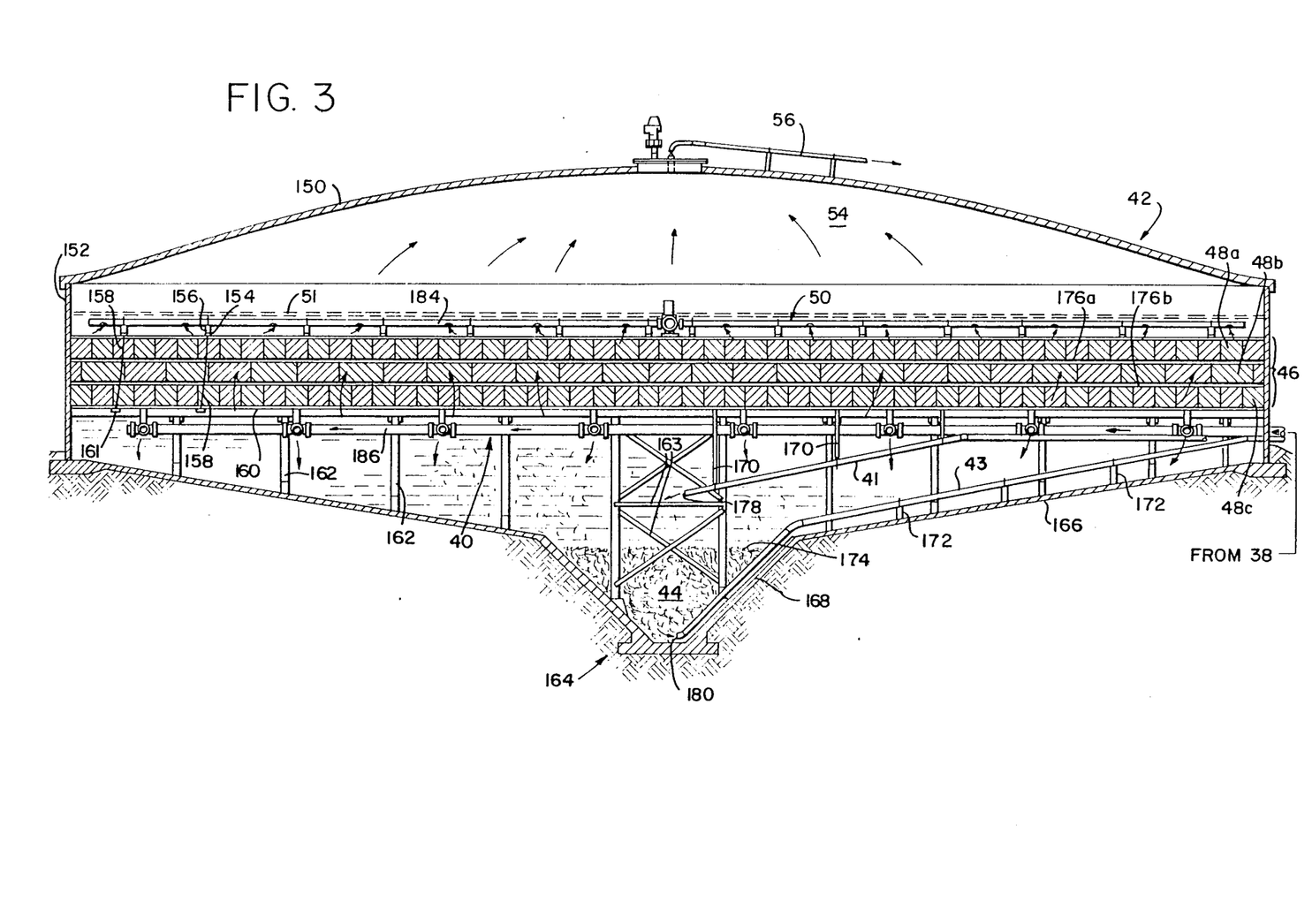
FIG. 3 is a side, sectioned view of the anaerobic reactor as shown in FIGS. 1 and 2.

The details of construction of the anaerobic reactor 42 are shown in FIGS. 2 and 3. The enclosure for the anaerobic reactor 42 includes a dome 150, supported by a cylindrically shaped side wall 152, which in turn rests on a floor comprised of first and second conically shaped floors 166 and 168, as shown in FIG. 3. The lower edge of the side wall 152 rests on the first floors 166, which slopes down at a relatively gradual angle with respect to horizontal. In continuous fashion, the first floor 166 is joined with the second floor 168, which is oriented to form a greater angle with respect to horizontal. The bottom or storage portion 44 is formed by the second cylindrically shaped floor 168 to receive the sludge mass 174. As the sludge is introduced by the influent distribution conduit 41, it settles through the process wastewater onto the first floor 166, sliding down into the storage portion 44 formed by the second floor 168.

As particularly shown in FIG. 3, the media assembly 46 is comprised of the top media 48a, the middle media 48b and the lower media 48c separated by a first set of spacers 176a disposed horizontally as seen in FIG. 2, and a second set of spacers 176b disposed vertically as shown in FIG. 2. In some embodiments of this invention, the spacers 176a and 176b may not be needed. The wastewater introduced by the influent distribution conduit array 40 is forced up as shown by the arrows in FIG. 3. Each media 48 is made up of a plurality of sections, with adjacent sections having surfaces for directing the wastewater in opposite directions. After passing up through the media assembly 46, the wastewater is collected and withdrawn from the anaerobic reactor 42 by the effluent collection conduit array 50.

The media assembly 46 is supported directly on a plurality of support beams 160 disposed horizontally and substantially parallel with each other as shown in FIG. 2. Lateral beams 161 are disposed substantially parallel with each other and perpendicular to the support beams 160. A plurality of support members 162 is disposed in a vertical or upright position as shown in FIG. 3, having one end secured to the first or second floors 166 or 168, and their other end affixed to the lateral beams 161. Bracing members 163 are connected between adjacent upright support members 162 to enhance the rigidity of support provided to the media assembly 46.

As shown in FIG. 2 and 3, the reactor influent is introduced from the input conduit 38 into the influent distribution conduit array 40. The array 40 is comprised of a distribution header 186 disposed along a horizontal diameter of the cylindrically shaped side wall 52, as shown in FIG. 2. A plurality of coupling joints 190 is disposed at equal spacings along the length of the distribution header 186, whereby the reactor effluent is distributed to a plurality of distribution laterals 188 extending on both sides of the header 186 in substantially parallel relationship to each other, whereby the reactor effluent is evenly introduced across a cross section of the anaerobic reactor 42 as taken through its cylindrical side wall 152.

The structure of the effluent collection conduit array 50 for collecting the reactor effluent is best shown in FIG. 2, as comprising a collector header 182 disposed along a diameter of the cylindrically shaped side wall 152 in a horizontal orientation. A plurality of coupling joints 185 is evenly spaced along the length of the distribution headers 186 and serve to couple fluid from a plurality of collector laterals 184 extending on either side of the collector header 182 and in substantially parallel relationship to each other, whereby effluent is collected uniformly over a cross sectional area of the anaerobic reactor 42. As best shown in FIG. 1, the reactor effluent is withdrawn via the collector header 182 and a coupling conduit 53 to be discharged via the output 52 to the outlet conduit 64.

Each collector lateral 184 is supported, as shown in FIG. 2, by a pair of lateral braces 155 extending horizontally as shown in FIG. 2. A plurality of lateral supports 154 is disposed along the length of each pair of lateral braces 155, the lateral support 154 extending in a vertical direction as shown in FIG. 2. As shown in FIG. 3, each lateral support 154 includes a support post 156 extending upright as shown in FIG. 3 to receive and secure as by a metal strap, its collector lateral 184.

Figure 4:
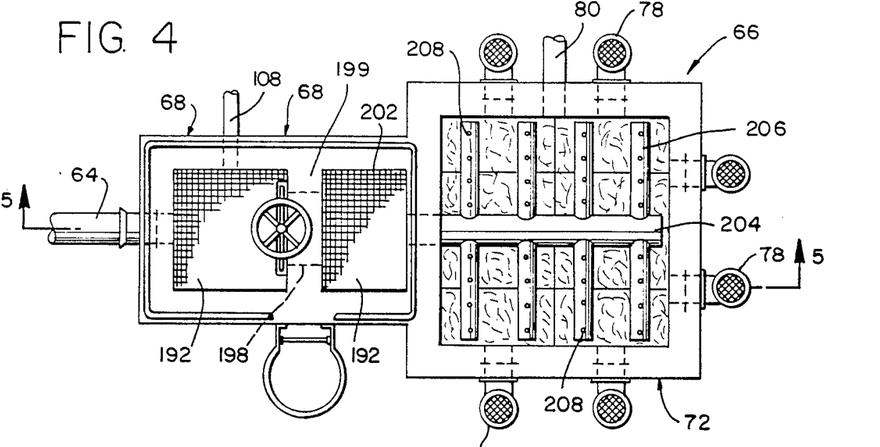
FIGS. 4 and 5 are respectively a plan view and a side, sectioned view of the degassification chamber as shown in FIG. 1.
Figure 5:
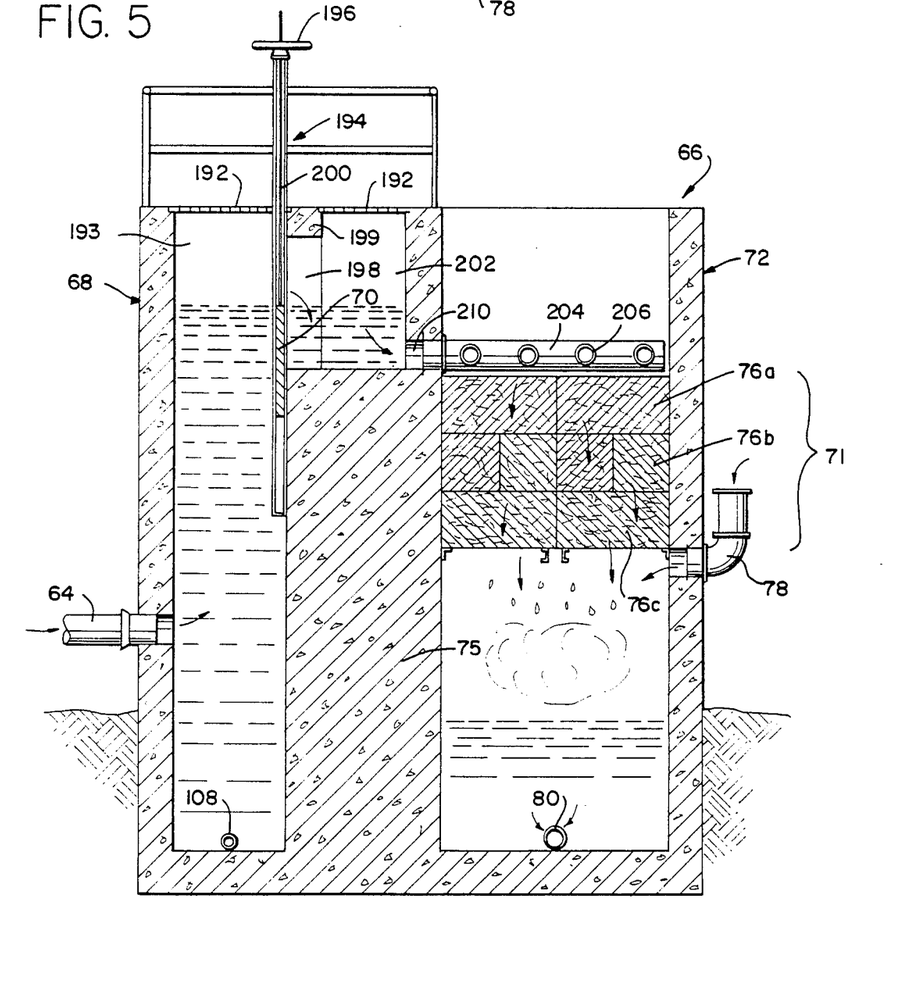

The details of the structure of the degassification chamber 66, as generally shown in FIG. 1, are best shown in FIGS. 4 and 5. The reactor effluent is introduced via outlet conduit 64 into the degassification chamber 66 and, in particular, to its wet well 68. The degassification chamber 66 is divided by a partition into the wet well 68 and the degassing chamber 72. The wet well 68 includes a first chamber 193 for receiving water to a level set by the topmost edge of the effluent weir 70. The height of the effluent weir 70 is controlled by a weir gate control system comprised of a wheel 196 affixed to a threaded rod 200. By rotating the wheel 196 in one direction or the other, the effluent weir 70 may be effectively raised and lowered, respectively. A partition 199 separates the receiving chamber 193 from a reservoir 202. A window 198 is formed within the partition 199 to permit the reactor effluent to flow over the topmost edge of the effluent weir 70 and into the reservoir 202. A pair of gratings 192 respectively cover the chamber 193 and the reservoir 202. The recirculating conduit 108 is disposed in communication with a bottom portion of the receiving chamber 193 to permit the reactor effluent to be directly recirculated via the sludge pumping station 112 to the anaerobic reactor 42.

The reactor effluent passes through the reservoir 202 to be discharged to the degassing chamber 72, which receives the media assembly 74. The reactor effluent flows through an outlet opening 210 and into a distribution manifold 204 from which lateral pipes 206 extend on either side. A plurality of equally spaced orifices 208 is disposed, as shown in FIG. 4, on the top side of the lateral pipes 206 to permit substantially even distribution of the reactor effluent across the cross sectional area of the media assembly 74. A plurality of the discharge openings 78 is disposed about the sides of the degassing chamber 72. The conduit 80 is disposed in communication with a lower portion of the degassing chamber 72 to direct the degassed effluent to the clarifier 84, as shown in FIG. 1.

The loading or flow rate of the reactor effluent over the media assembly 74 of the degassification chamber 66 is illustratively set at 5 gallons per minute per sq. foot of the cross sectional area of the media assembly 74. If the load rating is set too small, bacterial slime will grow on the media surfaces. On the other hand, if the loading rate is increased significantly, the efficiency of gas release will be reduced.

The efficiency of the wastewater treatment process within the anaerobic reactor 42 depends upon maintaining the proper conditions within the reactor 42, namely maintaining the reactor contents within the mesophilic range and of maintaining the desired bacterial population in terms of the ratio of the mass of the food waste present in the raw wastewater, to the mass of the available microorganisms. Under proper environmental conditions, the anaerobic fermentation taking place in the anaerobic reactor 42 converts a significant portion of the organic waste constituents into methane and carbon dioxide via a two step process of (1) dehydrogenation and decarboxylation of complex organic molecules by acidophilic bacteria to form short chain volatile fatty acids, followed by; (2) methanogenesis to produce methane and carbon dioxide. The process reaction rate is controlled by the growth rate of the methanogen bacteria necessary for the second step.

Under normal conditions, anaerobic waste treatment proceeds with a minimum of control. However, sudden and dramatic changes in loadings or environmental conditions, e.g. a temperature change of 1° F., can cause the process to become unbalanced. It is important to determine this "unbalance" condition early so that control measures can be introduced before process performance is significantly affected. Although no single parameter or test will indicate the onset of unbalanced conditions, the most important test for process control is that for determining the concentration of volatile acids, as discussed above. This test gives an indication of the volatile acids formed as intermediate compounds during the treatment process. The methane forming bacteria are responsible for the destruction of volatile acids, and if they become affected by adverse conditions, their rate of utilization will slow down and the volatile acids concentration will increase. The volatile acid test allows the monitoring of the balance between the production of acids or intermediate compounds and the further production of methane. A high volatile acids concentration in itself is not harmful, but indicates that some other factor is affecting the methane bacteria.

It is in the second stage of methane fermentation that real waste stabilization occurs. During this stage, the organic acids are converted by a special group of bacteria termed "methane formers" into carbon dioxide and methane. Different methane forming organisms are responsible for the anaerobic treatment for different waste. The different methane formers develop at significantly different rates, thus requiring a start-up period until all the groups of methane formers are finally established. There are also many different acid forming bacteria. Waste stabilization requires a balance among all of these organisms. The establishment and the maintenance of the balance between the first and second steps is indicated by the concentration of the volatile acids. When the system is in balance, the methane bacteria use the acid intermediates as rapidly as they appear. However, if operating conditions change notably, e.g. an increase of waste products, the concentration of all of the acids will also increase. In accordance with the teachings of this invention, the detection of a change of operating conditions and, in particular, the increase of volatile acid, will indicate such an imbalance, such that the pump 142 is then actuated to introduce bicarbonate from the alkalinity slurry system 138. The bicarbonate is introduced in sucn quantities so as not to change directly the pH of the reactor contents, but rather to promote the activity of the methane producers. By promoting the activity of the methane formers, the concentration of the volatile acids is reduced.

In operating the anaerobic reactor 42, waste loads from the food processing plant may vary significantly from weekdays to weekends. Under these transient loading conditions, the volatile acids concentration starts low at the beginning of the processing shift at the beginning of the week. The volatile acids level then increase tor the first few days of the processing period as volatile acid production exceeds methanogenesis. Typically the volatile acids concentration levels off in a few days and tends to decrease towards the end of the week.

Changes in the percentage of carbon dioxide in the reactor 42 may sometimes indicate the onset of unbalanced condition; an unbalanced treatment often results in decreased methane production which is accompanied by an increase in carbon dioxide percentage. Carbon dioxide is measured by entering the conduit 56 through a door (not shown) and measuring the percentage of carbon dioxide therein by a device known as a "Fyrite" as manufactured by the Bacharach Instrument Company of Pittsburgh, Pa. The percentage of carbon dioxide for a given waste product is known. For example, for the illustrative example as described above of food products, 20 to 25% of the gas produced by the anaerobic reactor 42 is carbon dioxide, the remainder being methane. For typical domestic waste water, the percentage of carbon dioxide is 40%. It is noted that at least 55% of the output needs to be methane in order to support burning within the boiler 58. If the measured percentage of carbon dioxide changes from a known, normal range, there is an indication of an unbalanced treatment within the anaerobic reactor 42. Another indication of unbalanced conditions is a decrease in the efficiency of operation.

Temporary unbalanced conditions are the result of sudden changes in temperature, organic loading or the nature of the wastes. The heat exchangers 24 and 34 are operated to maintain a constant operating temperature in the anaerobic reactor 42. Because of the volume of water contained in the anaerobic reactor 42, it would be difficult to suddenly change its temperature once the anaerobic reactor 42 is in operation. Temporary unbalances in the variation of volatile acids during the production week are related to the adjustment of the bacteria to the new conditions. What is needed to control these temporary conditions is time for adjustment. By providing optimum environmental conditions and controlling pH, a temporary unbalanced condition will soon correct itself.

Because of the various chemical equilibria existing in an anaerobic system, pH control can be difficult unless the factors affecting pH are understood. At the near neutral pH of interest for anaerobic treatment, the major chemical system controlling pH is the carbon dioxide-bicarbonate system. The bicarbonate alkalinity is approximately equivalent to the total alkalinity when the volatile acid concentration is low. As the volatile acids increase, they are neutralized by the bicarbonate alkalinity, forming volatile acid alkalinity. If an increase in the volatile acid concentration decreases the bicarbonate alkalinity too much, a serious drop in pH can occur. Providing a bicarbonate alkalinity level sufficient to act as a buffer for temporary increases in volatile acids is the key to maintaining proper pH levels in the system. As a minimum, the bicarbonate alkalinity should be kept at 1,000 mg/l in the reactor effluent. A bicarbonate alkalinity in the 2,000 to 2,500 mg/l range will provide much more "buffer capacity" so that larger increases in volatile acids can be handled with a minimum drop in pH.

Rather than using sodium hydroxide or lye to adjust pH, soda ash, sodium bicarbonate, or sodium sesquicarbonate will be used to adjust the alkalinity in the anaerobic reactor 42 and therefore prevent pH reduction problems. By maintaining sufficient bicarbonate alkalinity, variations in volatile acids associated with weekday and weekend loading differences will not cause an unbalanced condition by reducing the reactor pH. For processing the food distribution plant as described above for a five day per week duty cycle, the amount of volatile acids typically increases from the first through the third day of operation. For example, 50 mg/l may be present on the first day increasing to as much as 250 mg/l on the third day of production. Beginning on the third day, there will be a decrease of volatile acids due to the normal processing within the reactor 42 to convert these acids to methane. As the ratio approaches 0.2, it may then become necessary to activate the alkalinity slurry system 138 and introduce sodium bicarbonate into the reactor 42. It is noted that keeping the alkalinity range in the order of 2000 to 2500 mg/l will increase its buffering capacity to the point that the ratio may exceed 0.2. However, cost may be minimized by reducing the quantities of slurry bicarbonate introduced into the reactor 42, while closely monitoring the volatile acids-/alkalinity ratio, i.e. keeping it below 0.2. The illustrative chemicals selected for this process offer several other advantages over lime and sodium hydroxide. They do not react with carbon dioxide to create a vacuum in the anaerobic reactor 42 as lime does. They are easy to handle, and can be added to give high alkalinity levels without producing any adverse or toxic effects.

The successful control of the anaerobic process of this invention depends upon an understanding of the various environmental factors which affect the microorganisms responsible for waste degradation. Of the various factors, pH is one of the most important to control. This control is dependent upon operating the bicarbonate alkalinity buffering system 138 to neutralize the volatile acids produced during the treatment process. The feed rate of bicarbonate is adjusted to maintain the alkalinity within the previously mentioned range.

Thus, there has been shown and described an improved wastewater treatment system that carries out an anaerobic process wherein bacteria consume waste materials in an anaerobic digestion process to produce methane and carbon dioxide as bi-products. The anaerobic digestion process is carried out at controlled conditions, namely the temperature is maintained within the mesophilic range of 85° to 100° F. and the pH of the contents of the anaerobic digester is maintained at 6.8 to 7.2. The anaerobic wastewater treatment system of this invention is economic to operate in that it requires no extra energy source. A supplemental heater using heated cooling water from a food processing plant heats the digester influent during operating times of the food processing plant, whereas at all times a primary heater uses the methane given off by the anaerobic digestion process as its source of fuel to heat the reactor influent. Further, the reactor influent is introduced at a point below the media assembly, thus forcing the influent up through the media. Biological sludge produced is removed in a clarifier and introduced into a bottom, storage portion of the reactor. The longer the sludge solids are retained in the storage portion, the bacteria present in the digester continues its anaerobic digestion process, thus reducing the solid materials that would need to be disposed of and, further, providing a source of bacteria during system start-up. As operating conditions change and in particular as the waste load increases, the production of the volatile acids increases. To counterbalance the increased acid production, bicarbonate from the alkalinity slurry system is introduced into the digester to buffer its contents, thus promoting the activity of the methane bacteria to use up the volatile acids and to bring the process into balance. Further, the reactor effluent may be circulated back into the anaerobic reactor to provide a warm but dilute bacteria source. Alternatively, a sludge, i.e., a solution dense in bacteria but relatively cool, may be recirculated and reintroduced into the anaerobic reactor. The construction of the anaerobic reactor and in particular its bottom storage portion within the earth provides additional insulation tending to maintain the storage contents at even temperature and to minimize the requirements for additional heating. A degasser is used to remove entrained gas in the reactor effluent, thus, facilitating the settling of sludge in the clarifier.

In considering this invention, it shoulc be remembered that the present disclosure is illustrative only and the scope of the invention should be determined solely by the appended claims.

I claim as my invention:
1. Anaerobic apparatus for treating wastewater, said apparatus comprising:
   (a) a reactor for receiving and treating the wastewater in an anaerobic process, said reactor having a bottom and a top;
   (b) media disposed within said reactor having a plurality of surfaces for receiving bacteria, which consume the waste in the wastewater by an anaerobic digestion process to produce methane and a biological sludge;
   (c) storage means disposed in said bottom for storing biological sludge;
   (d) first means for introducing the wastewater into said reactor at a point intermediate said media and said bottom, whereby the wastewater is forced up and over said surfaces of said media and into contact with the bacteria;
   (e) second means disposed at a point intermediate said top and said media for withdrawing the treated wastewater;
   (f) settling means coupled to said second means for receiving the treated wastewater and for permitting settlement of the biological sludge to a bottom thereof, said bottom coupled by a conduit to introduce the biological sludge into said storage means, whereby the population of the methane gas producing bacteria within said reactor is increased and the efficiency of the anaerobic digestion process within said reactor to produce methane is improved;
   (g) degassing means coupled to said second means to receive and degas the reactor effluent and is coupled to said settling means to supply degassed reactor effluent thereto, whereby the efficiency of the biological sludge settlement within said settling means is improved;
   (h) third means disposed in communication with said storage means for withdrawing the biological sludge from said reactor; and
   (i) means disposed at said top for collecting the methane.

2. The anaerobic apparatus as claimed in claim 1, wherein there is further included heater means coupled to said collecting means to receive the collected methane for burning said methane to heat the wastewater directed to said first means.

3. The anaerobic apparatus for treating the waste of a plant also providing heated water as a bi-product, as claimed in claim 2, wherein there is included a second conduit coupled to said first means for feeding the wastewater into said reactor, said first mentioned heater means disposed in proximity to said second conduit to heat the wastewater passing through said second conduit, and second heater means disposed in proximity to said second conduit and coupled to receive the heated water for heating the wastewater passing through said second conduit.

4. The anaerobic apparatus as claimed in claim 1, wherein said first-mentioned conduit is coupled in communication with said first means for transporting and introducing the biological sludge from said settling means through said first means into said reactor, a second conduit coupled to said second means and to said first means for transporting and introducing the reactor effluent via said first means into said reactor, and control valve means for controlling the flow of the biological sludge from said settling means or the reactor influent to be introduced via said first means into said reactor.

5. The anaerobic apparatus as claimed in claim 1, wherein there is included means responsive to the buildup of volatile acids in said reactor for introducing via said first means a quantity of bicarbonate sufficient to neutralize said volatile acids and enchance the activity of the methane producing bacteria.

6. The method of operating an anaerobic apparatus comprising:
   (a) a reactor for receiving and treating wastewater in an anaerobic process, said reactor having a bottom and a top;
   (b) a medium disposed within said reactor having a plurality of surfaces for receiving bacteria, which consume the waste in the wastewater by an anaerobic digestion process to produce methane and biological sludge; and
   (c) storage means disposed in said bottom for storing biological sludge, the method comprising the step of:
      1. heating the wastewater to a temperature of 85° to 100° F.;
      2. thereafter, introducing the heated wastewater into said reactor at a point intermediate said media and said storage means;
      3. directing the wastewater up and over said surfaces of said media and into contact with the bacteria to produce methane in accordance with the anaerobic digestion process;
      4. withdrawing the wastewater after a hydraulic detection time at a point intermediate said top and said media;
      5. treating the withdrawn wastewater from the reactor to remove gas therefrom, to enhance the settlement of the biological sludge substantially unimpeded by the presence of gas in the reactor effluent;
      6. permitting sludge to settle from the withdrawn wastewater; and
      7. introducing a selective amount of the settled sludge into and storing the sludge in said storage means of said reactor for a solids retention time in excess of said hydraulic detection time, whereby the population of the methane gas producing bacteria within said reactor is increased and the efficiency of the anaerobic digestion precess to produce methane is enhanced.

7. The method of operating the anaerobic apparatus as claimed in claim 6, wherein there is further included the step of introducing an alkaline substance in an amount sufficient to promote the anaerobic digestion activity, but insufficient to change the pH of the wastewater within said reactor.

8. The method of operating the anaerobic apparatus as claimed in claim 7, wherein the amount of alkaline substance is introduced to maintain the wastewater in said reactor at a minimum level of 1,000 milligrams per liter thereof.

9. The method of operating the anaerobic apparatus as claimed in claim 8, wherein the effluent drawn from said reactor is tested as to the quantities of volatile acids and alkaline substances therein and the ratio thereof obtained.

10. The method of operating the anaerobic apparatus as claimed in claim 9, wherein alkaline substances are introduced into said reactor sufficient to maintain a ratio of volatile acids to alkaline substances of not more than 0.2.

11. Anaerobic apparatus for treating wastewater, said apparatus comprising:
(a) a reactor for receiving and treading the wastewater in an anaerobic process wherein bacteria concume the waste in the wastewater by an anaerobic digestion process to produce methane and a biological sludge, said reactor having a bottom and a top;
(b) storage means disposed in said bottom for storing the biological sludge;
(c) first means for introducing the wastewater into said reactor at a point above said bottom, whereby the wastewater is forced up and into contact with the bacteria;
(d) second means disposed at a point intermediate said top and said first means for withdrawing the treated water;
(e) degassing means coupled to said second means for receiving the reactor effluent and for removing gas therefrom, said degassing means being exposed to atmospheric pressure and including media and means for directing a flow of the reactor effluent over said media, whereby the reactor effluent is directed as a thin film downward through said degassing means to efficiently release gas therein;
(f) settling means coupled to said degassing means for receiving the degassed reactor dffluent and for permitting the efficient settling of the biological sludge to a bottom thereof substantially unimpeded by the presence of gas in the reactor effluent;
(g) a conduit coupled to a bottom portion of said settling means for receiving and transporting therethrough the settled biological sludge and for introducing the biological sludge into said storage means; and
(h) means disposed at said top for collecting the methane.

12. The anaerobic apparatus as claimed in claim 11, wherein said conduit is coupled to said first means.

13. The anaerobic apparatus as claimed in claim 11, wherein said reactor includes third means disposed in communication with said storage means for introducing biological sludge into said storage means, said conduit coupled to said third means.

* * * * *